US009937215B2

(12) United States Patent
Walbroel et al.

(10) Patent No.: US 9,937,215 B2
(45) Date of Patent: Apr. 10, 2018

(54) PREPARATIONS WITH ROSEHIP EXTRACTS, AND METHOD OF PRODUCING ROSEHIP EXTRACTS

(75) Inventors: Bernd Walbroel, Königswinter (DE); Björn Feistel, Andernach (DE); Ivo Pischel, Rossbach (DE)

(73) Assignee: Finzelberg GmbH & Co., KG, Andernach (DE)

( * ) Notice: Subject to any disclaimer, the term of this patent is extended or adjusted under 35 U.S.C. 154(b) by 0 days.

(21) Appl. No.: 12/808,969

(22) PCT Filed: Dec. 19, 2008

(86) PCT No.: PCT/EP2008/068081
§ 371 (c)(1),
(2), (4) Date: Oct. 20, 2010

(87) PCT Pub. No.: WO2009/080778
PCT Pub. Date: Jul. 2, 2009

(65) Prior Publication Data
US 2011/0135721 A1    Jun. 9, 2011

(30) Foreign Application Priority Data

Dec. 21, 2007  (EP) .................................... 07123943

(51) Int. Cl.
| | |
|---|---|
| *A61K 9/64* | (2006.01) |
| *A61K 36/00* | (2006.01) |
| *A23G 4/06* | (2006.01) |
| *A23L 2/385* | (2006.01) |
| *A23L 2/395* | (2006.01) |
| *A61K 31/7008* | (2006.01) |
| *A61K 31/737* | (2006.01) |
| *A61K 36/738* | (2006.01) |
| *A61K 38/01* | (2006.01) |
| *A61K 38/39* | (2006.01) |
| *A61K 45/06* | (2006.01) |
| *A23L 29/281* | (2016.01) |
| *A23L 33/105* | (2016.01) |

(52) U.S. Cl.
CPC .............. *A61K 36/00* (2013.01); *A23G 4/068* (2013.01); *A23L 2/385* (2013.01); *A23L 2/395* (2013.01); *A23L 29/281* (2016.08); *A23L 33/105* (2016.08); *A61K 31/7008* (2013.01); *A61K 31/737* (2013.01); *A61K 36/738* (2013.01); *A61K 38/014* (2013.01); *A61K 38/39* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,004,976 A | | 1/1977 | Isaac |
| 5,595,743 A | * | 1/1997 | Wu ............................... 424/728 |
| 5,997,888 A | * | 12/1999 | Weder et al. .................. 424/401 |
| 6,024,960 A | | 2/2000 | Kharazmi et al. |
| 6,485,752 B1 | | 11/2002 | Rein |
| 6,800,433 B1 | | 10/2004 | Honda et al. |
| 2004/0224906 A1 | | 11/2004 | Hoving et al. |
| 2006/0177525 A1 | | 8/2006 | Takagaki et al. |
| 2007/0154575 A1 | * | 7/2007 | Shimoda et al. ............. 424/756 |
| 2009/0061027 A1 | | 3/2009 | Pandalis |
| 2010/0119630 A1 | | 5/2010 | Feistel et al. |
| 2011/0135721 A1 | | 6/2011 | Walbroel et al. |
| 2011/0300244 A1 | | 12/2011 | Pischel et al. |

FOREIGN PATENT DOCUMENTS

| | | |
|---|---|---|
| CN | 1 928 098 | 3/2007 |
| DE | 202006004872 U1 | 7/2006 |
| EP | 1 071 439 B1 | 1/2001 |
| EP | 1837029 A1 | 9/2007 |
| FR | 2 897 238 A1 | 8/2007 |
| JP | 06-336421 A | 12/1994 |
| JP | 2001-072583 A | 3/2001 |
| JP | 2001-278792 A | 10/2001 |
| JP | 2004113141 A | 4/2004 |
| JP | 2007-261987 A | 10/2007 |
| RU | 2240131 C1 | 11/2004 |
| RU | 2355240 C1 | 5/2009 |
| WO | 92/15314 A1 | 9/1992 |
| WO | 99/53934 A1 | 10/1999 |
| WO | 00/64883 A1 | 11/2000 |
| WO | 03/043613 A2 | 5/2003 |
| WO | 2007110133 A1 | 10/2007 |
| WO | 2008/003314 A1 | 1/2008 |
| WO | 2008006589 A2 | 1/2008 |

OTHER PUBLICATIONS

Oesser and Seifert (Cell Tissue Res (2003) 311:393-399).*
Cheryan (Ultrafiltration and Microfiltration Handbook, CRC Press, 1998).*
Gao (J Sci Food Agric 80:2021-2027).*
McAlindon (Arthritis & Rheumatism, vol. 39, No. 4, Apr. 1996, pp. 648-6656).*
Schreiber (Chapter 4 of Gelatine Handbook: Theory and Industrial Practice, Wiley-VCH Verlag GmbH & Co. KGaA, published online Apr. 2007, pp. 301-309).*
Conner (Nutrition vol. 12, No. 4, 1996, pp. 374-377).*
Zheng (J. Agric. Food Chem. 2000, 48, 895-900).*
Salminen (Journal of Chromatography A, 1077 (2005) 170-180).*
Bragt, Inflammation, vol. 4, No. 3, 1980.*
Al'ter, "Use of the enzyme pectinase in the preparation of cholosas", Aptechnoe Delo, 6(3):50-2 (1957) Abstract.
Callard, "I feel it in my fingers . . . ", Natural Products (online article), Jul. 20, 2007, XP-002543525 (9 pages).
(Continued)

*Primary Examiner* — Devang K Thakor
(74) *Attorney, Agent, or Firm* — Christensen, Fonder, Dardi & Herbert PLLC; Peter Dardi

(57) ABSTRACT

Composition comprising an anti-inflammatory plant extract from rosehips together with a cartilage-protective substance, and a method of producing the rosehip extract.

23 Claims, No Drawings

(56) References Cited

OTHER PUBLICATIONS

Chrubasik et al., "A systematic review on the Rosa canina effect and efficacy profiles", Phytotherapy Research: PTR, 22(6):725-733 (Jul. 2008).
Chrubasik et al., "The evidence for clinical efficacy of rose hip and seed: a systematic review", Phytotherapy Research: PTR, 20(1):1-3, (Jan. 2006).
Deliorman Orhan et al., "In vivo anti-inplammatory and antinociceptice activity of the crude extract and fractions from *Rosa canina* L. fruits", J. of Ethnopharmacology, 112(2):394-400 (Jul. 13, 2007).
Gao et al., "Evaluation of antioxidant activities of rosehip ethanol extracts in different test systems", J Sci Food Agric, 80(14):2021-2027 (2000).
"Joint and Bone Combo", necombo.wordpress.com, Nov. 10, 2007, author unknown (4 pages).
"Joint Flex 1000 with Chondroitin & Rosehip", vita.com/products.aura/HEPE10452.asp, 2000, author unknown (2 pages).
Kharazmi et al., "Rose hip inhibits chemotaxis and chemiluminescence of human peripheral blood neutrophils in vitro and reduces certain infalmmatory parameters in vivo", Inflammopharmacology, 7(4):377-386 (Jan. 1, 1999).
Lee et al., "Purification and Concentration of Betalaines by Ultra Filtration and Reverse Osmosis", Journal of Food Science, 47(2):465-471 and 475 (1982).
Munoz et al., "Effects of enzymatic treatment on anthocyanic pigments from grapes skin from chilean wine", Food Chemistry, 87(4):487-490 (Oct. 2004).
Novotel'Nov et al., "Enzymic preparation of vitamin C concentrate enriched with vitamin P", Biokhimiya (Moscow), 14:398-404 (1949) (1 page) Abstract.
Oszmianski et al., "Possible use of enzymatic preparations in the production of cloudy juices of high vitamin content from fruits of the rose Rosa rugosa; rosehip pectin degradation and juice preparation with high ascorbic a cid content", Chemical Abstracts Service, Columbus, OH 1993 (1 page) Abstract.
Shmeleva et al., "Effect of vitamins C+P complex on lactic acid *Streptococci* and the activity of its bacteriphage", 24(7):16-19 (1963) (1 page) Abstract.
Brief et al., "Use of Glucosamine and Chondroitin Sulfate in the Management of Osteoarthritis," J Am Acad Orthop Surg 2001; 9:71-78.
Rein et al., "A herbal remedy, Hyben Vital (stand. powder of a subspecies of *Rosa canina* fruits), reduces pain and improves general wellbeing in patients with osteoarthritis—a double-blind, placebo-controlled, randomised trial," Phytomedicine 11 (2004) 383-391.
Oesser et al., "Einfluss von Kollagenfragmenten auf Neusynthese und Degradation der extrazellulären Knorpelmatrix," Orthopädische Praxis 41, 10 (2005) 565-568. (See English language summary).
Joachimove, Skeletin se letos urcite hodi, ocekáváme "ohen v kostech", Energy Magazin, Apr. 2006 (Apr. 2006), http://www.energy.sk/cv/info/0604/0604.asp#6.
Energy Group S.A., "Product Documentation—SKELETIN", retrieved Apr. 17, 2013 (Apr. 17, 2013), www.energy.sk/files/2_vyrobky/PD_skeletin_EN_web.pdf.
Energy Group S.A., "Skeletin", http://web.archive.org/web/20070622074115/ http://www.energy.sk/info/vyrobky/skeletin.asp, Jun. 22, 2007 (Jun. 22, 2007), retrieved Mar. 24, 2014.
Ameye et al., "Osteoarthritis and nutrition. From nutraceuticals to functional foods: a systematic review of the scientific evidence", Arthritis research & Therapy, 8, pp. R127, Jul. 19, 2006.

Office Action from Canadian Patent Application No. 2,710,116 dated Apr. 22, 2013 (3 pages).
Office Action from Canadian Patent Application No. 2,710,116 dated Apr. 7, 2014 (3 pages).
Product Information for GorVita Artrevit, http://gorvita.com.pl, Szczawa, Malopolskie, Poland.
Product Documentation for Skeletin, produced by Energy Group, a.s., Prague, Czech Republic.
Google Search Results provided by the European Patent Office for the expression "Artrevit" within the time period of Jan. 1, 2000 through Dec. 12, 2007.
Google Search Results provided by the European Patent Office for the expression "Skeletin" within the time period of Jan. 1, 2000 through Dec. 12, 2007.
Office Action for corresponding European Patent Application No. 08865898.4, dated Nov. 29, 2012.
Hakansson et al, "Rose Hip and Lactobacillus plantarum DSM 9843 Reduce Ischemia/Reperfusion Injury in the Mouse Colon," Dig Dis Sci 51:2094-2101 (2006).
Translation of Notice of Rejection for corresponding Japanese Patent Application No. 2010-538774, dated May 28, 2013.
Blank, "Cistus Incanus Extract Relives Sore Throat", Deutsche Apotheker Zeitung, Deutscher Apotheker Verlag, Stuttgart, DE, 145(46):40-41 (Nov. 17, 2005).
Demetzos et al., "Hétérosides polyphénoliques des feuilles de Cistus creticus L," Ann. pharmaçeutiques françaises, 47(5):314-318 (1989).
Demetzos et al., "A New Labdane-Type Diterpene and Other Compounds from the Leaves of *Cistus incanus* ssp. Creticus," Journal of Natural Produxts, 53(5):1365-1368 (1990).
Droebner et al., "CYSTUS052, a polyphenol-rich plant extract, exerts anti-influenza virus activity in mice," Antiviral Research, 76:1-10 (2007).
Ehrhardt et al., "A polyphenol rich plant extract, CYSTUS052, exerts anti influenza virus activity in cell culture without toxic side effects or the tendency to induce viral resistance," Antiviral Research, 76:38-47 (2007).
Guvenc et al., "Antimicrobial Studies on Turkish Cistus Species," Pharmaceutical Biology 43(2):178-183 (2005).
HOC, "Extract from Cistus in canus against influenza pandemic?" Zeitschrift Fuer Phytotherapie, Hippokrates Verlag in MVS Medizinverlage, DE, 28(3):142-143 (2007).
Kroyer et al., "Evaluation of bioactive properties of pollen extracts as functional dietary food supplement," Innovative Food Science & Emerging Technologies, 2(3):171-174 (2001).
Kupeli et al., "Flavonoids with anti-inflammatory and antinociceptice activity from *Cistus laurifolius* L. leaves through bioassay-guided procedures," Journal of Ethnopharmacology, 112:524-530 (2007).
Richter, "Rock Rose (Cistus) cortra dysentery. Ancient knowledge revisited," MMW Fortschritt der Medizin, Urban und Vogel Medien und Medizin Verlagsgesellschaft, DE, 142(47):47-48 (2000).
Saracini et al., "Simultaneous LC-DAD and LC-MS Determination of Ellagitannins, Falvonoid Glycosides, and Acyl-Glycosyl Flavonoids in *Cistus salvifolius* L. Leaves," Chromatographia, 62(516):245-249 (2005).
Wetherall et al., "Evaluation of Neuraminidase Enzyme Assays Using Different Substrates to Measure Susceptibility of Influenza Virus Clinical Isolates to Neuraminidase Inhibitors: Report of the Neuaminidase Inhibitor Susceptibility Network," Journal of Clinical Microbiology, 41(2):742-750 (2003).
Yamaguchi et al., "Anabolic Effects of Bee Pollen Cistus ladaniferus Extract in Osteoblastic MC3T3-E1 Cells in Vitro," Journal of Health Science, 53(5):625-629 (2007).
Decision on Grant a patent for the invention from corresponding Russian Application No. 2010130339 with English translation, dated Jul. 11, 2014 (11 pages).

* cited by examiner

PREPARATIONS WITH ROSEHIP EXTRACTS, AND METHOD OF PRODUCING ROSEHIP EXTRACTS

RELATED APPLICATIONS

This application is a national stage filing of PCT Application No. PCT/EP2008/068081 filed Dec. 19, 2008, which is incorporated herein by reference and which claims priority to European Patent Application No. 07123943.8 dated Dec. 21, 2007.

The present invention concerns preparations with rosehip extracts and a method of producing rosehip extracts.

BACKGROUND OF THE INVENTION

More and more people are affected by osteoarthritis (joint wear, degenerative joint disease, arthrosis deformans). This illness is a rheumatic disease and in many cases—especially in acute phases—it is accompanied by painful inflammations. The pain is caused by the degeneration of joint cartilage. There are various factors which can lead to damage to cartilage. In addition to damage as a result of accidents, excessive stress on joints and congenital deformities of the joints, metabolic disorders, a lack of exercise and also an unhealthy diet are some of the major causes.

The starting point of each case of osteoarthritis is damage to the cartilaginous cover, the so-called "cartilage damage". Initially this damage is often limited to just a small area of a few square centimeters and it is also still only superficial. X-ray pictures show the first signs of the bone hardening a short time later and it is always areas of bone lying directly under the diseased cartilage which are affected. These additional changes to the bone are a conclusive sign of the early stages of osteoarthritis. Without these changes to the bone there is just "bone damage", not "osteoarthritis". Osteoarthritis thus always means cartilage damage with changes to the bone.

Osteoarthritis is a painful, chronic illness for the people affected and it impairs nearly all their activities. The consequences are pain, phases of inflammation, swelling, deformation and stiffening of the joints. The extent and manifestation of these phenomena can vary greatly for each joint and each stage, however. Freedom of movement is severely restricted.

In their search for some relief many patients turn to over-the-counter or prescription drugs, undergo protracted physiotherapy or even submit themselves to operations. All these treatments often provide only short-term relief from the pain, however. In most cases destruction of the cartilage continues inexorably with the result that the pain becomes worse and the limitations in movement more serious.

An inflammation (Latin: inflammatio) is a characteristic response of biological tissue to an irritation triggered externally or internally, and its function is to eliminate or repair the injurious irritation. An inflammation can be present in a localised area or as a systemic inflammation reaction. In this example arthritis is a major factor in determining the pain of osteoarthritis. With arthritis, the five signs of inflammation (reddening, excessive warmth, swelling, pain and limited function) can all be observed in most cases within its chronic course. The redness and excessive warmth, for example, are often a warning sign, even if a short one, of an incipient flare-up of inflammation which will soon be followed by the pain phase. With the joints often having widened already, the swelling is frequently hardly noticed any more. The limited function may then be regarded as the result of the pain and in marked forms as the result of malpositions.

There are thus two ways to combat inflammations caused by damage to cartilage and therefore to improve the pain situation and to reduce the joint stiffness for the patients:

The first approach involves the supportive self-healing of the body through cartilage-protective substances. Nutritional supplements with collagen hydrolysate for healthier and more functional joints are available on the market and can be used for this purpose. They serve to strengthen the collagen in the joint and to support its regeneration. In *Orthopädische Praxis* (2005, 10, 41: 565-568), Dr. S. Oesser describes the influence of the collagen fragments on the new synthesis and degradation of the extracellular cartilage matrix. The collagen hydrolysate used in this publication and in the examples of this application comes from type 1 collagen. This has a stimulating effect on the formation of the type 2 collagen as well as on pericellular proteoglycan biosynthesis. Type 2 collagen contains approximately 70% of the quantitatively most important component (of joint cartilage) and provides elasticity and strength. A study by Dr. Roland W. Moskowitz in *Semin Arthritis Rheum* (2000, 30: 87-99) concludes that a daily dose of 10 g collagen hydrolysate leads to a significant reduction in the pain suffered by arthritic patients.

Furthermore, preparations with glucosamine sulphate (daily dose of 0.75 g-1.5 g) and/or chondroitin sulphate (daily dose 0.4 g-0.8 g) are readily available which likewise claim to have a protective effect on the cartilage. A publication by A. A. Brief in *J. Am. Acad. Orthop. Surg.* (2001, 9: 71-78) documents a corresponding effect.

The second approach is the suppression of the inflammation and/or the reduction of inflammation mediators. These mediators, e.g. cytokines, produce a defence reaction which is too strong.

The natural reaction of the body to fight inflammation is to release corticoids. It therefore seemed reasonable to synthesise cortisol derivatives and to market these as anti-inflammatory drugs. Prednisolone and dexamethasone are still the last resort today as they are very powerful drugs. Long-term treatment leads to severe side effects, however, such as striae, muscular atrophy, changes to the blood count and diabetes mellitus type 2.

The preferred alternatives today for long-term therapy are non-steroidal antirheumatics (NSAR) and COX-2 inhibitors. Diclofenac, ibuprofen, indometacin and oxicame also have potential side effects, however, ranging from gastrointestinal problems to gastric ulcers and damage to the liver or kidneys.

Medicinal herbs found in naturopathy have been used in many civilisations for hundreds of years and they are noted for having very few, if any, side effects. The classically recognised phytopharmaceuticals include phyteuma, commonly known as rampion. While the active principle of, for instance, willow bark with salicin, appears to have been explained, much research is still being carried out into other plants.

Rosehip, as a classical food plant, has surprisingly emerged as a potent antiphlogistic. Rosehip is a compound fruit containing many small nuts. The fruit is harvested in late autumn. Its flesh comes from the fleshy bottom part of the fruit and is sweet and sour and rich in vitamins, in particular vitamin C (ascorbic acid) but also vitamins A, B1 and B2. Traditionally, rosehip is used as a substitute for vitamin C to treat colds and flu-like infections. Vitamin C also plays an important role in the regeneration of collagen in the joint cartilage and is necessary to keep bones and supporting tissue healthy. The U.S. Pat. No. 6,024,960 describes the correlation between a high vitamin C content and an anti-inflammatory effect of preparations made from rosehip. In the U.S. Pat. No. 6,485,752 B1, the combination of a rosehip concentrate with fish oil is protected which is aimed at a high vitamin C content in the extract and at unsaturated fatty acids in the fish oil.

According to reports, an improvement of movement and of well-being can be achieved by taking rosehip powder. A research group headed by Prof. Dr. Kharazmi at the University of Copenhagen studied the effects of a rosehip powder with joint-related arthritis problems in 2004 and isolated a galactolipid proportion using a "complicated fractionation process". The galactolipid "GOPO®" was patented in conjunction with the manufacturing process for rosehip powder (EP 1 071 439). It was able to be proven in vitro that this galactolipid inhibits the migration of polymorphonuclear leucocytes, and in vivo that it reduces the serum concentration of C-reactive protein (CRP). In a clinical study, the CRP value fell by an average of 39% after just 10 days. A placebo-controlled cross-over study was carried out with 112 patients suffering from osteoarthritis and a daily dose of 5 grams of rosehip powder (LitoZin®) was investigated. The study showed a significant alleviation of morning stiffness with 66% of those taking part in the study after taking the rosehip powder for three months. Additionally, in the dietotherapy with rosehip it was possible to reduce the consumption of pain-relief medication such as opioids, tramadol, paracetamol and NSAR by around half. The rosehip powder used in the product LitoZin® is standardised to a substance containing 175 ppm and may be described as inhomogeneous on visual inspection. This is revealed in varying particle sizes across multiple batches (coarse particle of 20% between 0.5-0.7 mm to ultrafine constituents of 40% between 0.05-0.2 mm). A systematic overview by C. Chrubasik et al. in *Phytotherapy Research* (2006, 20:1-3) summarises the clinical data on rosehip powders.

The rosehip powders used are poorly characterised and/or standardised. The amounts to be taken of up to 10 g are very large due to the low concentration of the active substances. There is thus still the need for characterised and/or standardised rosehip products exhibiting a high level of effectiveness per unit of weight.

The task of the present invention is to provide an easily tolerated agent which is anti-inflammatory and which in particular can be used to treat joint problems and joint-related illnesses.

The task is solved by means of a composition containing an anti-inflammatory plant extract from rosehip together with a cartilage-protective substance.

DETAILED DESCRIPTION OF THE INVENTION

The aim of the invention was to develop an extract from a little used food plant to combat or to prevent inflammation reactions. It should preferably be an extract preparation which is combined with cartilage-protective drying agents during or after the drying process. Additionally, an extract should be developed that is effective without constituents which are excessively sensitive to temperature (galactolipids), which have side effects (salicylates), which are sensitive to oxidation (ascorbic acids) or are purely lipophilic (triterpene acids).

The way rosehip works may be described as follows: leucocytes "attracted" by cytokines are involved in the inflammatory process in the joints. It was surprisingly found that the inventive rosehip extract reduces the release of the cytokines so that fewer leucocytes migrate to the area of inflammation and damage the cartilage tissue further.

However, the cartilage tissue is also damaged through the formation of free radicals from the inflammation process. It was surprisingly found that the rosehip extract described in the invention also reduces this build-up of free radicals irrespective of its natural ascorbic acid content. By doing so the inventive rosehip extract diminishes the inflammation reaction in the joints or even suppresses it completely. This stops damage to and destruction of the cartilage, and not only is the pain relieved but movement is also improved.

The invention describes the production and use of an extract from rosehip as well as its combination with cartilage-protective substances such as collagen hydrolysate, glucosamine and/or chondroitin sulphate for maintaining health and/or reducing symptoms in the case of rheumatic problems, especially in the case of chronic joint inflammation illnesses such as rheumatoid arthritis and similar illnesses. An embodiment particularly preferred is the use of a cartilage-protective substance as a direct drying agent for the rosehip extract.

In a preferred embodiment, a rosehip extract is used which can be obtained through a method for the production of a dry extract made from rosehip using the following steps:
  a) Extraction of rosehip (*Rosa canina*) with water or a mixture of water and up to 50% by mass of ethanol in order to obtain a simple extract
  b) Purification of the simple extract obtained using at least one of the steps
    b1) enzymatic fermentation
    b2) membrane filtration
  c) Drying of the extract The skin of the rosehip or the skin and the seeds of the rosehip can be used.

Fructus Cynosbatum DAB or Cynobastum sine semine is preferred for use as a drug.

Surprisingly, it has been possible to develop an extract which is pre-treated in an embodiment with the aid of an enzyme. Enrichment of the active principle also needed to be achieved in another embodiment using the method of selective membrane filtration. The treatment of enzymes and membrane filtration can also be combined.

It was surprising to find that a vacuum drying process in a temperature range of up to 80° C. did not have an adverse effect on the activity.

Hydrolytic enzymes in particular, and especially glycosidases, have proven to be effective for enzymatic treatment. Other suitable enzymes are cellulases, such as hemicellulases and especially xylanases. Enzymes which are particularly preferred for use are pectinases.

Membrane filtration is a process in which filtration is through a membrane and which enables even the smallest particles to be removed. The preferred method of membrane filtration is ultrafiltration, whereby substances can be removed on account of their molecule size and the permeate continues to be used. Suitable exclusion sizes for the membranes were at 1 kDa to 500 kDa, even more preferably at 10 kDa to 300 kDa, especially at 100 kDa.

Synergistic effects in the reduction of pain and the duration of the manifestation of the symptoms were able to be observed through the support of the self-healing powers of the cartilage regeneration. An extract made from rosehip of the species *Rosa canina* is used. The preferred extract does not contain any detectable traces of the galactolipid "GOPO®" and contains only a rudimentary concentration of salicylates. The lipophilic pentacyclic triterpene acid content is also minimal.

The evidence of the dosage-dependant anti-inflammatory effect was shown in a study in which the inhibition of a lipopolysaccharide (LPS)-induced release of inflammatory mediators was measured on human monocytes. These were in particular the cytokines interleukin-1β (IL-1β), interleukin-6 (IL-6), prostaglandin $E_2$ ($PGE_2$) and the tumour necrosis factor-alpha (TNF-α). $PGE_2$ is one of the "main prostaglandins" involved in the inflammatory process. It increases vascular permeability (swelling of the tissue), is involved in the development of redness and increases the pain (which is caused by other inflammatory substances such as bradykinin or histamine) by sensitising nociceptive nerve endings.

A study showed that the inventive extracts, which did not contain GOPO®, which contained as little salicylate as possible and which also contained pseudosaponin-minimised aqueous extracts, had a very good anti-inflammatory effect.

If the regeneration of joint collagen was now accelerated by adding cartilage protectives such as collagen hydrolysate, glucosamine or chondroitin sulphate, it was possible to support the self-healing process of damage to the cartilage; this would enable the long-term consequences such as those of osteoarthritis to be reduced.

A purely aqueous yet more active rosehip extract was able to be developed in an embodiment. It can be shown that this extract manages without heat- and light-sensitive compounds of the galactolipid substance group, contains practically no salicylates prone to causing side effects, and is not dependent on the class of compounds of the lipophilic pseudosaponins.

These anti-inflammatory effects can be combined according to the invention with the cartilage-protecting and regeneration-promoting components of the collagen hydrolysate, glucosamine or chondroitin sulphate. Another preferred embodiment is the combination of the inventive extract with collagen hydrolysate to treat osteoarthritis and a calcium supplement in the form of calcium pyruvate.

Usage as a nutritional supplement and in well-balanced diets is possible; the target groups are those with chronic joint inflammation in order to reduce the quantities of NSAR used, as well as athletes to accelerate regeneration during rehabilitation phases after spraining joints and excessive stress on the intervertebral discs.

An additional object of the invention is a composition containing an anti-inflammatory plant extract together with cartilage-protective substances. Suitable anti-inflammatory plant extracts are extracts made from common horsetail, African plum, amaranth, angelica, arnica, comfrey, basil, club moss, wild garlic, Chinese bellflower, borage, nettle, blackberry, broccoli, buckwheat, buttercup, capsicum, curcuma, cucurbita, sweet violet, veronica, verbena, gentian, tarragon, eucalyptus, galingale, clove, ground elder, goldenrod, elder, ginger, camomile, nasturtium, cardamom, cherry, coriander, liquorice, lemon grass, lime flower, bay leaf, mangosteen, meadowsweet, marjoram, milk thistle, horseradish, lemon balm, mint, feverfew, olive, perilla, pepper, marigold, rosemary, sage, yarrow, candytuft, cowslip, celery, mustard, white willow, thyme, violet, chickweed, knotgrass, woodruff, willow bark, wormwood, hyssop, cinnamon, rock rose, onions and mixes of these.

Such extracts are suitable for medicines, food products or supplements for the prevention or reduction of symptoms with chronic joint inflammation, rheumatoid arthritis, arthritis, rheumatic illnesses, spondylitis, osteoarthritis and fibromyalgia, or to support rehabilitation after spraining joints or strain on the intervertebral discs.

EXAMPLES

Example 1: The Influence of the Extractant on the Anti-Inflammatory Potential of Cynosbati Extracts Two extracts were produced from each 1 kg of rosehip skin (*Rosa canina*) using 6 liters of solvent for each and at 50° C. for the duration of 6 hours. The extracts were left to settle overnight, combined and filtered until clear the following morning. The eluate was then evaporated to a solvent-free soft extract and dried in a vacuum at 50° C. with 50% maltodextrin. The extracts obtained were tested on human monocytes for their potential to inhibit typical inflammation parameters such as TNF-alpha or typical pain parameters such as PGE2.

| Extractant | PGE2 IC50 [µg/ml] | TNF-alpha IC20 [µg/ml] |
| --- | --- | --- |
| 70% EtOH V/V | 450 | 200 |
| 45% EtOH V/V | 200 | 100 |
| 20% EtOH V7V | 300 | 325 |
| Water | 450 | 100 |
| Water- PEG 300 | 450 | 200 |
| Water - Glycerol | 450 | 300 |
| Drug powder | >>500 | 350 |

The cynosbati drug powder has an unspecific, hardly measurable inhibition of PGE2. In contrast, extracts, especially aqueous or aqueous-ethanolic extracts, were measurable depending on the dosage. A mean 50% inhibition (IC50) was already measurable from 200 µg/ml (an effect which was at least 5 times stronger).

Furthermore, the extracts show a considerably increased, likewise dosage-dependent effect with the inhibition of the pain parameter TNF-alpha. As the drug powder achieved a maximum inhibition of 20%, the IC20 value was used by way of comparison.

Example 2: Purification Through Enzymatic Treatment

Two extracts were produced from 1 kg of rosehip skin using 6 liters of water for each at 50° C. The extracts were left to settle overnight, combined and filtered until clear the following morning. After adding 3 g Ultrazym® per 2 kg of dry matter, the extract was fermented at room temperature over the course of 2 days. Precipitates were separated from the solution by means of filtration. The supernatant was then evaporated to a soft extract (native extract yield 29%) and dried in a vacuum at 50° C. with 50% maltodextrin.

| | Aqueous extract | Aqueous extract after fermentation |
| --- | --- | --- |
| PGE2 - IC50 [µg/ml] | 450 | 400 |
| TNF-a - IC20 [µg/ml] | 100 | 50 |

The fermented extract was characterised through its content of 10.5% polyphenols; ascorbic acids, however, were not able to be measured (<0.04%). The pentacyclic triterpene acid content was below the limit of detection (<10 ppm) and no linolenic acids released by hydrolysis were able to be detected (no galactolipid GoPo®; <10 ppm). The anti-inflammatory potential of the purified extract was able to be increased by 50% with TNF-alpha.

Example 3: Purification with Membrane Filtration

The aqueous soft extract from example 1 was diluted with osmosis water to a dry matter content of 20% and separated into two fractions using an ultrafiltration exclusion size of 100 kDa. They were then evaporated to a soft extract and dried in a vacuum with 50% maltodextrin at 50° C.

|  | Starting extract | Permeate | Retentate |
| --- | --- | --- | --- |
| PGE2 - IC50 [µg/ml] | 450 | 350 | >>500 |
| TNF-a - IC20 [µg/ml] | 100 | <50 | 300 |

With the purification used according to the invention via ultrafiltration, the anti-inflammatory potential of TNF-alpha was able to be increased by over 50%. It was also possible to increase the PGE2 activity by over 50%. The extract did not contain any lipophilic substances (e.g. the galactolipid GoPo®<10 ppm). The active principle, in the form of water-soluble compounds, was able to be enhanced further through selective separation on a defined membrane filter.

Example 4a: Preparation of a Dry Extract with the Aid of Cartilage-Protective Drying Agents A soft extract of rosehip skin obtained according to the extraction conditions of example 1 with the extracting agent ethanol 30% V/V resulted in a native extract yield of 38%. After removing the solvent in a vacuum, the aqueous extract solution underwent enzymatic purification in accordance with example 2 and a native extract quantity of 31% was obtained. This extract solution was diluted with osmosis water to a dry matter content of 30%, and was homogenised whilst stirring with 50% collagen hydrolysate of type 1 (Gelita Sol D) and spray dried. It produced a reddish-beige coloured dry powder. The extract did not contain any lipophilic substances (e.g. the galactolipid GoPo®<10 ppm), was completely soluble in water and had a pleasant, berry-like taste.

Example 4b: Preparation of a Dry Extract with the Aid of Cartilage-Protective Drying Agents A soft extract of rosehip skin, obtained according to the extraction conditions of example 1 with the extracting agent water resulted in a native extract yield of 45%. After removing the solvent in a vacuum, the aqueous extract solution underwent enzymatic purification in accordance with example 2 and a native extract quantity of 38% was obtained. This extract solution was diluted with osmosis water to a dry matter content of 30%, and was homogenised whilst stirring with 30% collagen hydrolysate of type 1 (Gelita Sol LDA) and dried in a vacuum. It produced a reddish-beige coloured dry powder. The dry extract with 4.8% residual moisture did not contain any lipophilic substances (e.g. the galactolipid GoPo®<10 ppm; total fat 0.08%), was completely soluble in water and had a pleasant, berry-like taste. The ascorbic acid content was 0.1%. The total amount of protein was 31.8% (of which 5.1% nitrogen) according to nutritional value analyses pursuant to ASU [the official digest of test procedures], Section 64 LFGB [the German Food and Feed Code]. The carbohydrate content came to 57.7/100 g, which resulted in a calorific value of 1525 KJ/100 g.

Examples of use for the inventive extract:

Example 5: Extract of Thyme with Collagen Hydrolysate

Two extracts were exhaustively produced from 1 kg dried and chopped thyme (herba thymii) using 8 liters of purified water for each at 80° C. for the duration of 8 hours. The eluates were filtered off via the drug, combined and finally filtered until clear through a sheet filter. The eluate was then evaporated in a vacuum to a soft extract, free of solvents, with the essential oil content being removed as much as possible. The aqueous extract solution then underwent membrane filtration.

This extract solution was concentrated in a vacuum to a dry matter content of approximately 40% and then underwent liquid-liquid treatment with n-heptane to remove all lipophilic substances such as wax, resin or other essential oils. The remaining aqueous phase was removed of roughly 10% lipophilic substances. The soft extract obtained after this resulted in a native extract yield of 25%.

This extract solution, adjusted to a dry matter content (DMC) of 32%, was mixed with 20% collagen hydrolysate (Gelita Sol LDA), homogenised whilst stirring and spray dried.

This resulted in a brownish-beige dry powder. The extract contained no essential oil (e.g. thymol<10 ppm), roughly 3% polyphenol (UV-VIS) and was completely soluble in water.

Example 6: Extract of Russian Tarragon with Collagen Hydrolysate

Two extracts were produced from 1 kg dried and chopped tarragon (Herba Artemisia drancunculoides) using 9 liters of purified water for each at 80° C. for the duration of 6 hours. The extracts were filtered off via the drug, combined and finally filtered until clear through a sheet filter. The eluate was then evaporated in a vacuum to a soft extract, free of solvents, with the essential oil content being removed as much as possible. The aqueous extract solution then underwent membrane filtration.

The soft extract obtained after this resulted in a native extract yield of 33%.

This extract solution was concentrated in a vacuum to a dry matter content of 30% and homogenised with 30% collagen hydrolysate (Gelita Sol LDA) whilst stirring and spray dried.

It resulted in a brownish-beige dry powder. The extract contained no essential oil (e.g. methyl eugenol<10 ppm), approximately 1% flavonoids according to HPLC and was completely soluble in water.

Example 7: Extract of Ginger with Collagen Hydrolysate and Glucosamine

Two extracts were produced from 1 kg dried and chopped ginger roots (Rhizoma Zingiberis officinalis) using 12 liters of ethanol for each at 45° C. for the duration of 4 hours. The extracts were filtered off via the drug, combined and gently evaporated in a vacuum to a dry matter content of roughly 20%. The native extract yield amounted to 10%.

A mixture of 80% polyvinylpyrrolidone (Kollidon 25) and 20% collagen hydrolysate (Gelita Sol LDA) was likewise dissolved in 50% ethanol to a dry matter content of 20%.

Afterwards, both solutions were weighed in a ratio of 1:4 and homogenised in portions with each other whilst stirring constantly. The ginger coprecipitate produced by bonding the temperature and acid-sensitive ginger spicy substances into the matrix of Kollidon and collagen hydrolysate was removed of the solvent in a vacuum and dried to a dry extract preparation. 200 mg of such a preparation was mixed with 400 mg glucosamine and processed to a homogeneous, free-flowing powder using a 0.5 mm sieve for comminution.

Example 8: Extract of Guinea Pepper with Collagen Hydrolysate and Chondroitin Two extracts were produced from 3 kg dried Guinea peppercorns (*Aframomum melegueta*) using 10 liters of ethanol for each at 50° C. for the duration of 8 hours. The extracts were filtered off via the drug and a sheet filter, combined and gently evaporated in a vacuum to a dry matter content of roughly 20%. The native extract yield amounted to 10%.

A mixture of 80% polyvinylpyrrolidone (Kollidon 25) and 20% collagen hydrolysate (Gelita Sol LDA) was likewise dissolved in 50% ethanol to a dry matter content of 20%.

Afterwards, both solutions were weighed in a ratio of 1:3 and homogenised in portions with each other whilst stirring constantly. The pepper coprecipitate produced was removed of the solvent in a vacuum and dried to a dry extract preparation. 100 mg of such a preparation was mixed with 200 mg glucosamine and processed to a homogeneous, free-flowing powder using a 0.5 mm sieve for comminution.

Example 9: Extract of Sage Leaves with Collagen Hydrolysate

Three extracts were produced from 1 kg dried and chopped sage leaves (*Salvia officinalis*) using 5 liters of 70% EtOH V/V for each at 50° C. for the duration of 4 hours. The extracts were filtered off via the drug, combined and finally filtered until clear through a sheet filter. The eluate was then evaporated in a vacuum to a soft extract, free of solvents, with the essential oils being collected separately.

Afterwards, the aqueous extract solution underwent membrane filtration.

The soft extract obtained after this resulted in a native extract yield of 31%.

This extract solution was concentrated in a vacuum to a dry matter content of 35% and homogenised with 40% collagen hydrolysate (Gelita Sol LDA) whilst stirring.

The essential oil which had been separated previously was also added again in this homogenisation process. The entire solution was spray dried.

It resulted in a brownish-beige dry powder. The extract contained 0.2% essential oil, approximately 5% polyphenol (UV-VIS) and was completely soluble in water.

Example 10: Chewable Tablets

The recommended daily dosage corresponds to 5 g drug powder per day. This corresponds to the drug-extract ratio 1:1 of the extract preparation according to example 4a and likewise a dosage of 5 g. As the classic form of tablets or capsules for swallowing is roughly 6 per day and might thus negatively affect compliance, administrations are preferred for several grams. A variant which is preferred in terms of taste is an aromatised chewable tablet. The recommended daily dosage is 4 tablets in accordance with the following formula:

1 chewable tablet (2 g) contains:

| | |
|---|---|
| Extract preparation in accordance with example 4a | 1.5 g |
| Sorbitol | 0.3 g |
| PEG 4000 | 0.15 g |
| Aroma | 0.03 g |
| Calcium behenate | 0.02 g |

Example 11: Chewing Gum 100 g chicle is powdered, mixed with 250 g sugar substitute isomalt and heated in an evaporating dish until the mixture softens. It is then worked thoroughly with the addition of 66 g cynosbati dry extract (in accordance with example 4b) and 33 g calcium pyruvate, and placed on a tile sprinkled with starch and kneaded until even. There can also be additional aromatisation in the previous step. Finally, it is rolled out into thin sheets and then cut into flat sticks whilst still warm by using a little starch powder to prevent the mixture from sticking to the tile. The chewing gum portions should weigh 2 grams and the portion contains roughly 300 mg of the cynosbati extract.

Example 12: Effervescent Granulate or Tablets

To make the effervescent tablets 600 g citric acid is mixed with 300 g sodium hydrogen carbonate and 100 g of the inventive cynosbati extract (of example 4a) and 100 g calcium pyruvate monohydrate. 50 g mannitol, 25 g of a fruit aroma, 5 g saccharin and 20 g sodium cyclamate are added to this mixture. Once homogenisation is completed, the mixture can be granulated or directly pressed into tablet form. 5 g granulate or a 5 g effervescent tablet is recommended 3-4 times a day as a single dose.

Example 13: Ready-to-Drink Forms

Due to the good level of solubility of the extract powder, a ready-to-drink preparation in the form of single-dose ampoules, or fluids and/or syrups with a dosage spoon can easily be produced as well, however. A daily dosage of 1.5 g of the inventive extract of example 4b is recommended for these types of liquid mixtures. As well as suitable flavoured additives, additives of calcium supplements or soluble collagen hydrolysates of type 1 are particularly suitable as combination partners.

The invention claimed is:
1. A composition comprising:
   (1) an anti-inflammatory plant solvent extract from a plant material consisting of rose hip peel; and
   (2) collagen hydrolysates,
   wherein the solvent extract is prepared by water extraction.
2. The composition according to claim 1, wherein said plant solvent extract from rose hip peel is obtainable by a process comprising the following steps:
   a) extracting rose hip peel with water;
   b) separating the extract mixture to obtain a soluble portion of the mixture separate from the solids to form a single solvent extract;

c) purifying the single solvent extract obtained by at least one of enzymatic fermentation or membrane filtration; and
d) drying the extract.

3. A process for preparing a dry extract from rose hip peel, comprising the following steps:
a) extracting rose hip peel with water;
b) separating the extract mixture to obtain a soluble portion of the mixture separate from the solids to form a single solvent extract;
c) purifying the single solvent extract obtained by at least one of enzymatic fermentation with hydrolytic enzymes or membrane filtration; and
d) drying the extract together with collagen hydrolysate.

4. An extract obtainable according to claim 3.

5. A method of using the composition of claim 1, comprising preparing a medicament or food supplement or a balanced diet comprising the composition of claim 1 for the prevention and reduction of symptoms in joint complaints.

6. A method of using the composition of claim 1, comprising administering the composition of claim 1 for the prevention and reduction of symptoms in chronic joint inflammation, diseases of the rheumatic spectrum, spondylitis, osteoarthritis, arthrosis, fibromyalgia or for supporting rehabilitation after joint sprain or intervertebral disk compression.

7. A medicament comprising the composition of claim 1 in the form of a tablet, chewing tablet, hard gelatin capsule, soft gelatin capsule, lozenge, stick, sachet or in the form of liquid dosage forms, such as single-dose ampoules, fluids and syrups.

8. A food supplement comprising the composition of claim 1 in the form of a tablet, chewing tablet, hard gelatin capsule, soft gelatin capsule, lozenge, stick, sachet or in the form of liquid dosage forms, such as single-dose ampoules, fluids and syrups.

9. A balanced diet comprising the composition of claim 1 in the form of a tablet, chewing tablet, hard gelatin capsule, soft gelatin capsule, lozenge, stick, sachet or in the form of liquid dosage forms, such as single-dose ampoules, fluids and syrups.

10. The composition according to claim 2, wherein the drying is effected together with at least 20% collagen hydrolysate.

11. The composition according to claim 1, wherein the plant solvent extract is from rose hip peels of rose hips without the seed.

12. The composition according to claim 1, wherein the plant solvent extract is from rose hip peel of *rosa canina*.

13. The composition according to claim 1, wherein the collagen hydrolysate is collagen hydrolysate type I.

14. The composition according to claim 1, wherein the plant solvent extract from rose hip peel comprises no detectable traces of galactolipid and insignificant amount of salicylates and/or lipophilic pseudosaponins.

15. The composition according to claim 2, wherein the exclusion sizes for the membranes were at 10 kDa to 300 kDa.

16. The process according to claim 3, wherein the dry extract from rose hip peel comprises no detectable traces of galactolipid and insignificant amount of salicylates and/or lipophilic pseudosaponins.

17. The process according to claim 3, wherein the exclusion sizes for the membranes were at 10 kDa to 300 kDa.

18. The process according to claim 3, wherein the collagen hydrolysate is collagen hydrolysate type I.

19. A medicament comprising the composition of claim 4 in the form of a tablet, chewing tablet, hard gelatin capsule, soft gelatin capsule, lozenge, stick, sachet or in the form of liquid dosage forms, such as single-dose ampoules, fluids and syrups.

20. A food supplement comprising the composition of claim 4 in the form of a tablet, chewing tablet, hard gelatin capsule, soft gelatin capsule, lozenge, stick, sachet or in the form of liquid dosage forms, such as single-dose ampoules, fluids and syrups.

21. A balanced diet comprising the composition of claim 4 in the form of a tablet, chewing tablet, hard gelatin capsule, soft gelatin capsule, lozenge, stick, sachet or in the form of liquid dosage forms, such as single-dose ampoules, fluids and syrups.

22. The process according to claim 3, wherein the extract is from rose hip peels of rose hips without the seed.

23. The composition according to claim 2 wherein the purification step is an enzymatic fermentation and wherein the enzyme used in the enzymatic fermentation is a glycosidase or a cellulose.

* * * * *